(12) United States Patent
     Orman (10) Patent No.: US 9,237,968 B1
(45) Date of Patent: Jan. 19, 2016

(54) WATER SPORTS EAR PLUG

(71) Applicant: Scott Alan Orman, San Diego, CA (US)

(72) Inventor: Scott Alan Orman, San Diego, CA (US)

( * ) Notice: Subject to any disclaimer, the term of this patent is extended or adjusted under 35 U.S.C. 154(b) by 402 days.

(21) Appl. No.: 13/787,512

(22) Filed: Mar. 6, 2013

Related U.S. Application Data

(60) Provisional application No. 61/644,870, filed on May 9, 2012.

(51) Int. Cl.
    *A61F 11/08* (2006.01)
    *A61F 11/10* (2006.01)

(52) U.S. Cl.
    CPC ........... *A61F 11/08* (2013.01); *A61F 11/10* (2013.01); *A61F 2011/085* (2013.01)

(58) Field of Classification Search
    CPC . A61F 11/08; A61F 2011/085; A61F 11/006; A61F 11/10; H04R 25/652; H04R 25/654; H04R 25/656; A61M 3/0283; A61M 3/0287; A61M 3/0295; A61M 2210/0662; A61M 2210/0668; A61B 1/227; A61B 1/2275
    See application file for complete search history.

(56) References Cited

U.S. PATENT DOCUMENTS

| | | | | |
|---|---|---|---|---|
| 2,437,490 A * | 3/1948 | Watson et al. | .............. | 128/867 |
| 2,719,523 A * | 10/1955 | Von Gierke | .............. | 128/864 |
| 2,737,953 A * | 3/1956 | Wiltein | .............. | A61M 35/003 141/297 |
| 2,879,768 A * | 3/1959 | Anderson | .............. | A61M 3/0283 604/37 |
| 3,123,069 A * | 3/1964 | Laisne et al. | .............. | 128/865 |
| 4,194,512 A * | 3/1980 | Foti | .............. | A61F 11/08 600/555 |
| 4,537,187 A * | 8/1985 | Scott | .............. | A61F 11/08 128/864 |
| 4,702,238 A | 10/1987 | Scott | | |
| 4,878,560 A * | 11/1989 | Scott | .............. | 181/130 |
| 5,364,343 A * | 11/1994 | Apolet | .............. | A61M 3/0283 239/124 |
| 5,488,961 A | 2/1996 | Adams | | |
| 5,819,745 A | 10/1998 | Mobley et al. | | |
| 5,881,729 A * | 3/1999 | Castillo | .............. | A61F 11/08 128/864 |
| 7,025,061 B2 | 4/2006 | Haussmann | | |
| 7,185,655 B1 * | 3/2007 | Redon | .............. | A61F 11/08 128/864 |
| 8,122,892 B2 * | 2/2012 | Johnson et al. | .............. | 128/865 |
| 2009/0173353 A1 * | 7/2009 | Purcell | .............. | A61F 11/10 128/865 |
| 2012/0302957 A1 * | 11/2012 | Vlodaver | .............. | A61F 11/00 604/151 |

* cited by examiner

*Primary Examiner* — Victoria J Hicks
*Assistant Examiner* — Kari Petrik
(74) *Attorney, Agent, or Firm* — One3 IP Management, P.C.; Justin G. Sanders; Jeromye V. Sartain (57) ABSTRACT

An ear plug provides, in the exemplary embodiment, an ear plug body adapted to fit against a cavum conchae of the ear and defining an outwardly opening main cavity therewithin. An inner end of the ear plug body is sized and configured for fitting into an ear canal of the ear, while a base of the main cavity defines a sound hole that extends down through each of the base and inner end. A chamber wall is positioned within and extends across the main cavity, forming a hollow air chamber in fluid communication with the sound hole capable of selectively clearing any water droplets that may enter the main cavity and obstruct the sound hole. In an alternate embodiment, the base of the main cavity provides an upwardly protruding sound hole body configured for elevating an opening of the sound hole a distance above the base.

19 Claims, 9 Drawing Sheets

WATER SPORTS EAR PLUG

RELATED APPLICATIONS

This application claims priority and is entitled to the filing date of U.S. Provisional application Ser. No. 61/644,870, filed on May 9, 2012 and entitled "Water Sports Ear Plug." The contents of the aforementioned application are incorporated by reference herein.

INCORPORATION BY REFERENCE

Applicant hereby incorporates herein by reference any and all U.S. patents and U.S. patent applications cited or referred to in this application.

BACKGROUND OF THE INVENTION

1. Field of the Invention

Aspects of this invention relate generally to ear plugs, and more particularly to a water sports ear plug configured for protecting a user's ear canal from coming into contact with water and wind, while also consistently allowing sound to pass therethrough.

2. Description of Related Art

Surfers, swimmers, water skiers, and others who are in substantial contact with water often encounter problems with water entering the ear canal. This is particularly troublesome when the water entering the ear canal is relatively cold or becomes cold as a result of wind. A person subject to repeated conditions of this nature may develop a condition commonly referred to as surfer's ear—the development of bony stenosis of the external ear canal due to diffuse exostoses.

The common solution for preventing water or other foreign objects or substances from entering a person's ear canal is an ear plug. However, in the desire to perform at the peak of one's ability in any sport, the majority of participants will reject the use of any equipment which impairs the participant's ability to perform in the sport. Such is the case when the use of an ear plug during water sports and activities prevents or inhibits the ability to hear sounds clearly. Again, failure to use ear plugs during such water activities can have health impairing consequences, and the surgery to repair such consequences is a gruesome solution to restore one's hearing.

The following art defines the present state of this field:

U.S. Pat. No. 4,537,187 to Scott is generally directed to an earplug particularly adapted for use by surfers and swimmers having a small hole therein which keeps out water but which allows the user to hear, said plug being made of a soft plastic having a density of less than 1 whereby said plug will float.

U.S. Pat. No. 4,702,238 to Scott is generally directed to an earplug for attenuating sound and providing a watertight seal at the auricle which is made of solid, closed cell, slow recovery foam having an external flange adapted to extend beyond the auricle, the surface of the plug being convex to reflect away sound, and having an inwardly extending conical portion fitting into the auricle or cavum conchae and the outer portion of the ear canal sealing off the meatus of the external ear canal without substantially penetrating the external ear canal. The closed cell foam provides a multitude of convex and concave surfaces which dramatically reflect, dissipate and attenuate sound waves.

U.S. Pat. No. 5,488,961 to Adams is generally directed to ear plugs for swimming, snorkeling, scuba diving and other water related activities that form a watertight seal within an individual's outer ear canals. The ear plugs have a lumen extending along the ear canal. A hydrophobic membrane extending across the lumen, which admits air into or out of the ear canal but blocks water, seals the ear against water but transmits air. This passage of air equalizes pressure across the plug, improves hearing with the ear plug in place, and prevents water contaminants, such as harmful infectious agents and pollutants, from entering the ear canal.

U.S. Pat. No. 5,819,745 to Mobley et al. is generally directed to a pressure regulating ear plug for regulating the rate of change of pressure inside an ear to minimize the pressure differential between the middle ear and a volume of the external ear cavity adjacent the ear drum, made of an ear plug adapted to fit tightly within the external ear cavity with no or minimal air leakage, and disposed within the ear plug is a pressure regulator with a slow leak rate. The pressure regulator is preferably made of a porous ceramic material.

U.S. Pat. No. 5,881,729 to Castillo is generally directed to an ear plug for preventing water and wind from entering the ear canal while allowing audible tones to pass therethrough. The ear plug is provided with an ear plug housing which is provided with an outer member and an inner portion. The outer member is adapted to reside in the outer ear of the user and an elongate tubular member having an exterior portion adapted to extend downwardly within the ear canal of the user. The ear plug is further provided with an ear plug insert. The ear plug insert is provided with a retaining member which is generally annular, a membrane which is made of a water impervious material and is adapted to allow audible tones to pass therethrough, and an insert housing which is generally annular. The insert housing is provided with a first end which is axially disposable in the interior portion of the elongate tubular member which is adapted to receive the first end of the insert housing. The insert housing is further provided with a second end which is adapted to circumferentially receive the retaining member with the membrane securely disposed between thereto, so as to axially enclose the second end of the insert housing thereby preventing water and wind from entering the ear canal while allowing audible tones to pass therethrough.

U.S. Pat. No. 7,025,061 to Haussmann is generally directed to a passive hearing protection earplug for being worn at least in part in the ear canal of a user, comprising a hard shell having an elasticity of from shore D 85 to shore D 65 and pulling means which are adapted for being manually operated by the user and which are provided at the outer end of said shell, said shell having an outer surface individually shaped according to the measured inner shape of the user's ear canal and outer ear. The shell has a size and an outer shape which are adapted to enable said shell to be manually moved, by seizing the pulling means, from a sound attenuation position into a communication position from which it is automatically returned into the attenuation position by elastic forces exerted by deformed parts of the user's ear canal and concha upon release of the pulling means. The invention also relates to a use of such an earplug and a method for manufacturing such an earplug.

In a bit more detail, and as illustrated by the above discussed prior art, while ear plugs have traditionally been designed to reduce or block out sound, there have been some approaches taken—including the '941 patent to Adams and the '729 patent to Castillo—to design ear plugs that allow sound to pass through, while blocking harmful elements of water and wind. However such ear plugs nevertheless tend to block too much of the sound to provide a satisfactory solution.

At least one attempt was made to solve this problem—namely, the '187 patent to Scott—by providing a small opening through a membrane such that sound is capable of passing through to the ear canal without any significant interference.

The opening is of such a size to allow sound to pass through, while still protecting the ear canal from exposure to the harmful elements of water and wind. While such a design works well for letting sound through when the ear plug is initially inserted into the ear, it fails in use when the user comes in contact with water. This failure is due to water droplets that often stick to the exterior of the small opening in the membrane, and thus occlude the sound from getting through. The only way to regain the original level of sound passing through the opening is to somehow dislodge the water droplets, usually through violent tapping on the ear plug until the droplets become dislodged. This is not only an irritation to the external parts of the ear, but also a dangerous habit as it can also cause damage to the ear canal due to the violent nature of striking the ear plug.

Thus, while the prior art described above teaches various types of ear plugs, it fails to teach an ear plug capable of protecting the user's ear canal from coming into contact with water and wind, while also consistently allowing sound to pass therethrough. Aspects of the present invention fulfill these needs and provide further related advantages as described in the following summary.

SUMMARY OF THE INVENTION

Aspects of the present invention teach certain benefits in construction and use which give rise to the exemplary advantages described below.

The present invention solves the problems described above by providing a water sports ear plug configured for protecting a user's ear canal from coming into contact with water and wind, while also consistently allowing sound to pass therethrough. The ear plug provides, in the exemplary embodiment, an ear plug body adapted to fit against a cavum conchae of the ear, the ear plug body defining a main cavity therewithin, opening outwardly away from the ear. An inner end of the ear plug body is sized and configured for fitting into an ear canal of the ear. A base of the main cavity defines a sound hole that extends down through each of the base and inner end of the ear plug body. A chamber wall is positioned within and extends across the main cavity, forming a hollow air chamber between the chamber wall and a side of the ear plug body, in fluid communication with the sound hole. Additionally, a selectively deformable top portion extends overtop of and encloses the air chamber. Thus, the air chamber is capable of selectively clearing any water droplets that may enter the main cavity and obstruct the sound hole.

In an alternate embodiment, the base of the main cavity provides an upwardly protruding sound hole body configured for elevating an opening of the sound hole a distance above the base, for assisting in substantially preventing any water droplets that may enter the main cavity from obstructing the opening.

A primary objective inherent in the above described apparatus and method of use is to provide advantages not taught by the prior art.

Another objective is to provide such an apparatus that protecting a user's ear canal from coming into contact with water and wind.

Another objective is to provide such an apparatus that consistently allows sound to pass therethrough, into the user's ear canal.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION OF THE INVENTION

The above described drawing figures illustrate aspects of the invention in at least one of its exemplary embodiments, which are further defined in detail in the following description.

Figure 1:
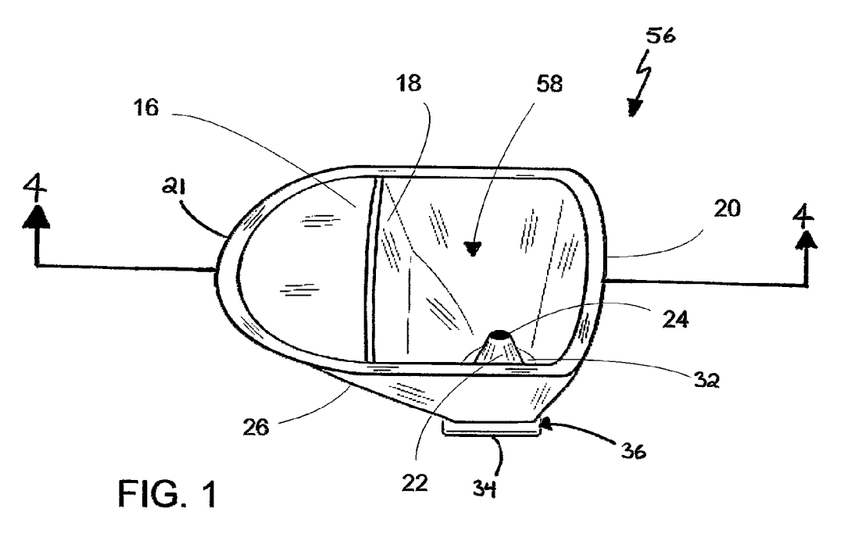
FIG. 1 is a top perspective view of an exemplary embodiment of the present invention.
Figure 3:
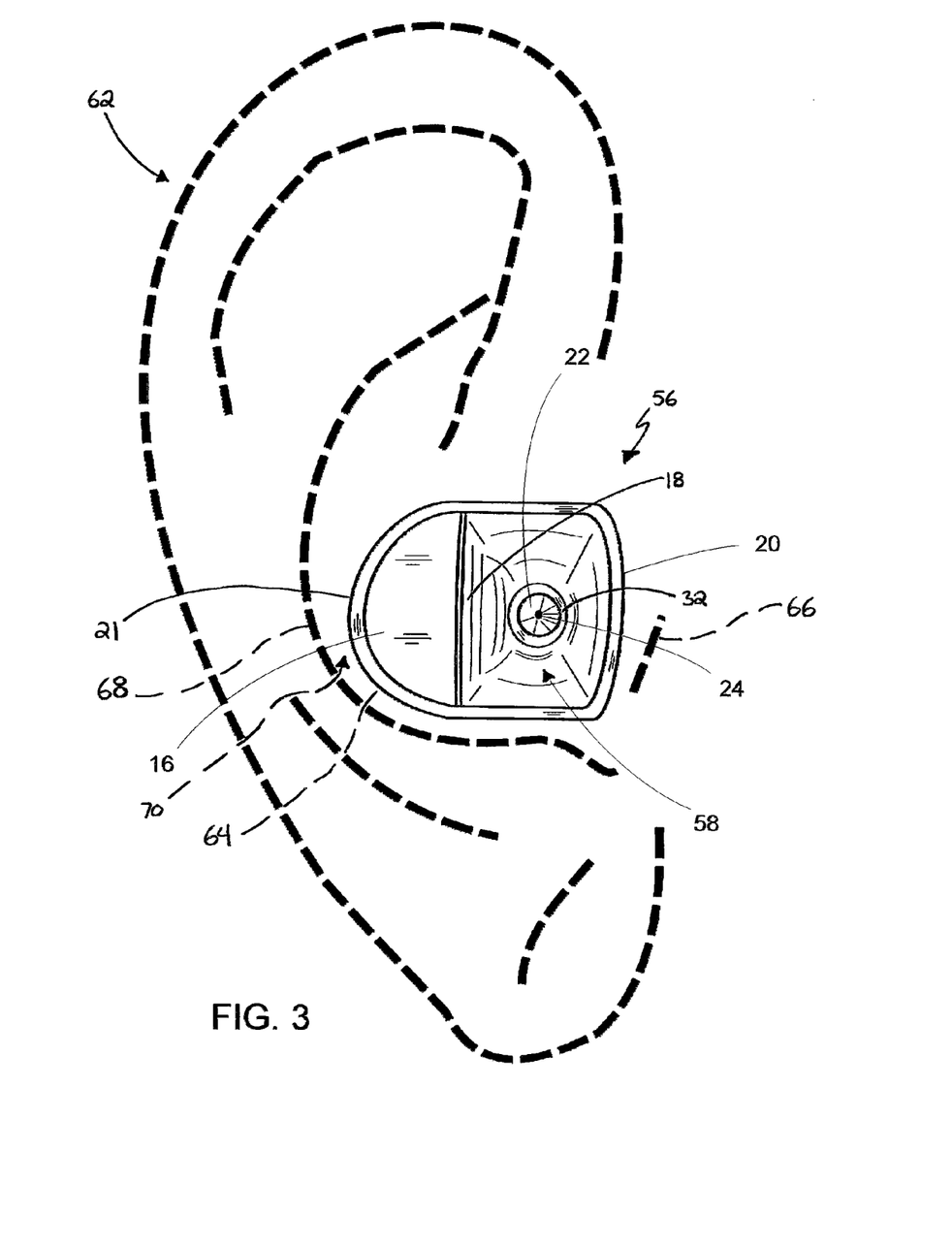
FIG. 3 is top plan view thereof, as seated in an ear of a user, in at least one embodiment.

Turning now to FIG. 1, there is shown a top perspective view of an exemplary embodiment of a water sports ear plug 56. The ear plug 56 comprises, in at least one embodiment, a substantially hollow, inwardly extending, conical-shaped ear plug body 26 adapted to fit against a cavum conchae 64 of an ear 62 of a user 60 when the ear plug 56 is selectively positioned within the ear 62 (FIG. 3). Additionally, when positioned within the ear 62, a first side 20 of the ear plug body 26 is adapted to rest against a tragus 66 of the ear 62, while an opposing second side 21 of the ear plug body 26 is adapted to rest against an antihelix 68 and concha 70 of the ear 62. However, in further embodiments, the ear plug body 26 may be sized and configured for fitting against other portions of the ear 62 without departing from the spirit and scope of the present invention.

In the exemplary embodiment, the ear plug 56 is made of a relatively soft, resilient plastic material, such as a styrene rubber copolymer sold under the trade name Kayton D #2104, and is manufactured using common injection molding processes known by those familiar in the art. However, in further embodiments, the ear plug 56 may be made of any material or combination of materials, now known or later developed, through any other method of manufacture, now known or later developed, capable of enabling the ear plug 56 to substantially carry out the functionality herein described.

With continued reference to FIG. 1, the ear plug body 26 defines a main cavity 58 therewithin, opening outwardly away from the ear 62 (when the ear plug 56 is positioned within the ear 62). Additionally a chamber wall 18 is positioned within and extends across the main cavity 58, defining a hollow air chamber 40 between the chamber wall 18 and a side of the ear plug body 26, separate from the rest of the main cavity 58. A relatively thin (or at least selectively deformable) top portion 16 extends overtop of and encloses the air chamber 40—the purpose for which is discussed further below. In the exemplary embodiment, the air chamber 40 is formed within the main cavity 58 between the chamber wall 18 and the second side 21 of the ear plug body 26 (i.e., adjacent the antihelix 68 and concha 70 of the ear 62). However, in further embodiments, the air chamber 40 may be positioned elsewhere within the main cavity 58. It should also be noted that, in at least one embodiment, each of the top portion 16 and chamber wall 18 is made of a relatively resilient material (such as a styrene rubber copolymer, for example), or combination of materials, for allowing the top portion 16 and chamber wall 18 to be selectively deformable—the purpose for which is discussed further below. However, in alternate embodiments, at least the chamber wall 18 may be made of a relatively rigid material or combination of materials.

Figure 2:
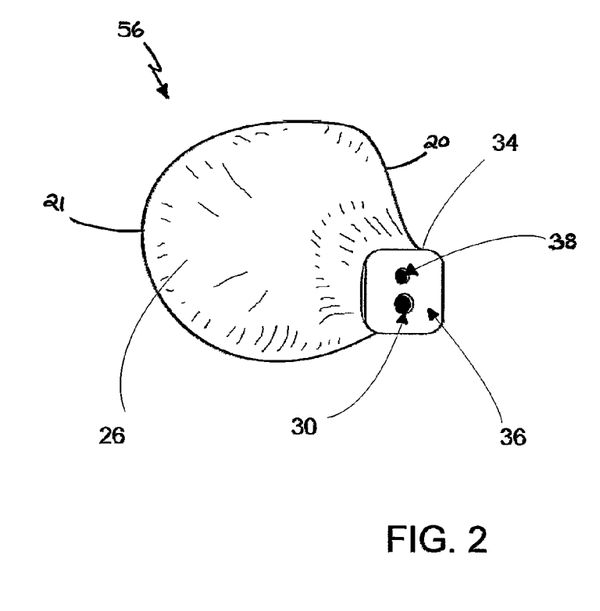
FIG. 2 is a bottom perspective view thereof, in at least one embodiment.
Figure 7:
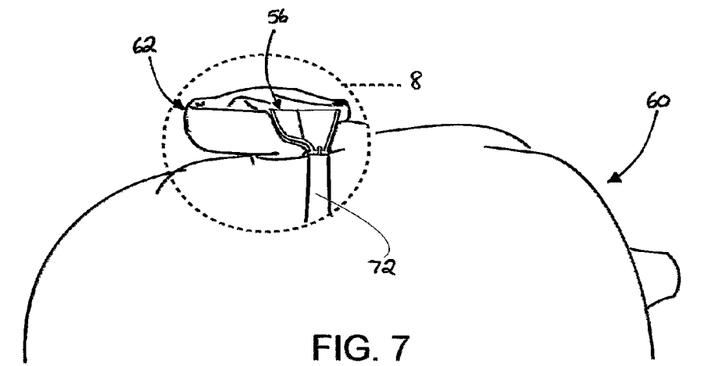
FIG. 7 is a further cross-sectional view thereof, as seated in the ear of the user, in at least one embodiment.
Figure 8:
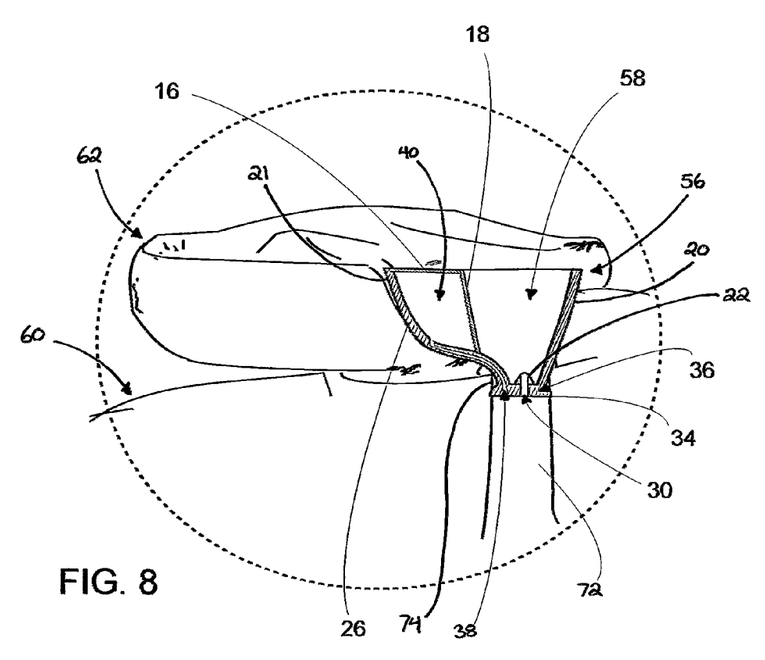
FIG. 8 is an enlarged view of a portion of the cross-sectional view of FIG. 7, in at least one embodiment.

As shown in FIGS. 1 and 2, an inner end 36 of the ear plug body 26 is sized and configured for fitting into an ear canal 72 of the ear 62, thereby occluding a meatus 74 of the ear canal 72 (FIGS. 7 and 8). In the exemplary embodiment, the inner end 36 is relatively flat; however, in alternate embodiments, the inner end 36 may be of any other shape or size, now known or later developed, capable of allowing the inner end 36 to substantially carry out the functionality herein described. As best shown in the cross-sectional view of FIG. 4, the inner end 36 also provides an at least one external flange 34, in at least one embodiment, sized and configured for snugly fitting into and frictionally contacting the ear canal 72 for better maintaining the ear plug 56 within the ear 62.

Figure 4:
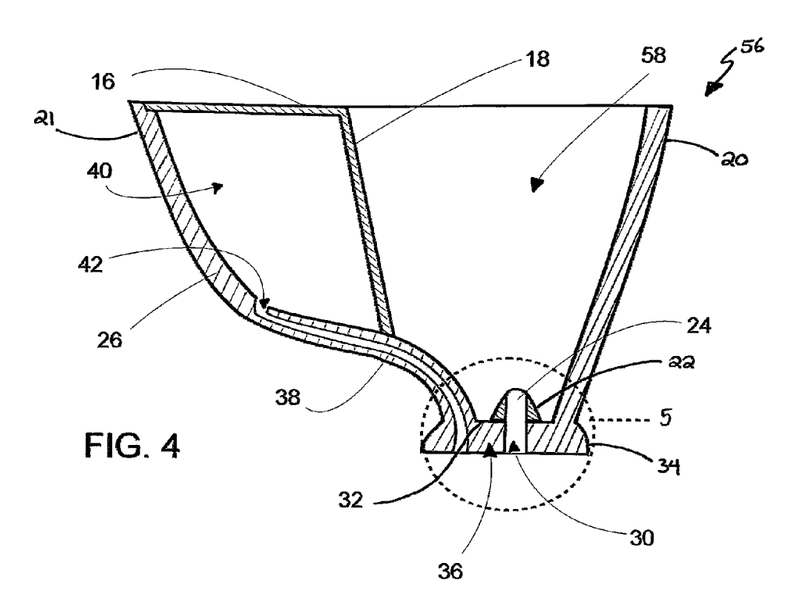
FIG. 4 is a cross-sectional view thereof, taken along line 4-4 in FIG. 1, in at least one embodiment.

With continued reference to FIGS. 1, 2 and 4, a base 32 of the main cavity 58, in at least one embodiment, provides an upwardly extending, substantially conical-shaped protuberance that forms a sound hole body 22. In the exemplary embodiment, the sound hole body 22 is approximately 3.0 millimeters in height; however, in alternate embodiments, the shape and dimensions of the sound hole body 22 may vary. The sound hole body 22 defines a sound hole 30 that extends down through both the sound hole body 22 as well as the base 32 and inner end 36 of the ear plug body 26, thereby allowing sound that may enter the main cavity 58 of the ear plug 56 to enter an opening 24 of the sound hole 30, pass through the sound hole 30 and into the ear canal 72. The sound hole 30 is preferably selected to be of such a size that it will normally keep out water, yet will offer little sound attenuation. It has been found that a diameter of approximately 0.762 millimeters is suitable for achieving such functionality. With a diameter of this size, the surface tension of water will normally keep it from passing through the sound hole 30, yet the sound hole 30 is still large enough to result in relatively little sound attenuation (5 dB or less) and provide a good level of hearing. Air naturally residing in the ear canal 72 also tends to exert a back pressure against any water at the sound hole 30 to keep it out. It should be noted, though, that the sound hole 30 may take on other dimensions in further embodiments, capable of allowing the sound hole 30 to substantially carry out the functionality herein described.

Figure 5:
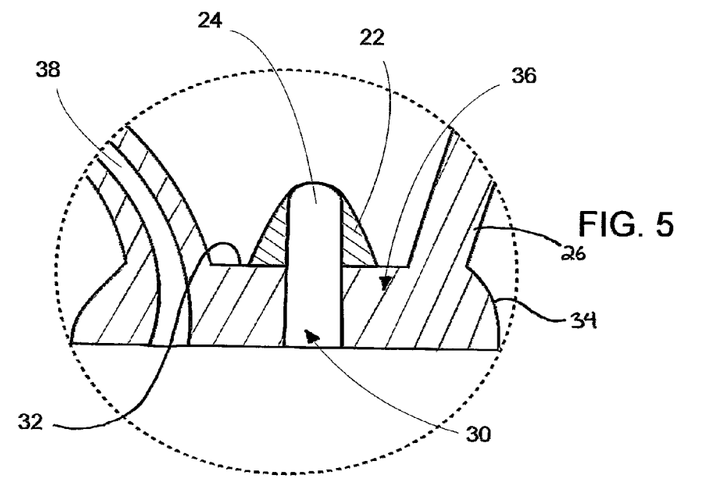
FIG. 5 is an enlarged view of a portion of the cross-sectional view of FIG. 4, in at least one embodiment.

While a sound hole 30 of the size described above is typically capable of preventing water from passing therethrough and into the ear canal 72, water droplets may nevertheless accumulate within the main cavity 58, around the sound hole body 22, and potentially cover the opening 24 of the sound hole 30. The dimensions of the sound hole body 22, as described above, assist in substantially preventing any water droplets from covering the opening 24 of the sound hole 30. However, the ear plug 56 is capable of clearing any water droplets that may nevertheless cover the opening 24 by virtue of the air chamber 40 being in fluid communication with the sound hole 30. Specifically, in at least one embodiment shown in the cross-sectional views of FIGS. 4 and 5, a chamber hole 42 positioned within the air chamber 40 is interconnected with an air channel 38 that extends down through the ear plug body 26 and out the inner end 36, allowing air to selectively travel from the air chamber 40 down into the ear canal 72, then up through the sound hole 30.

Figure 6:
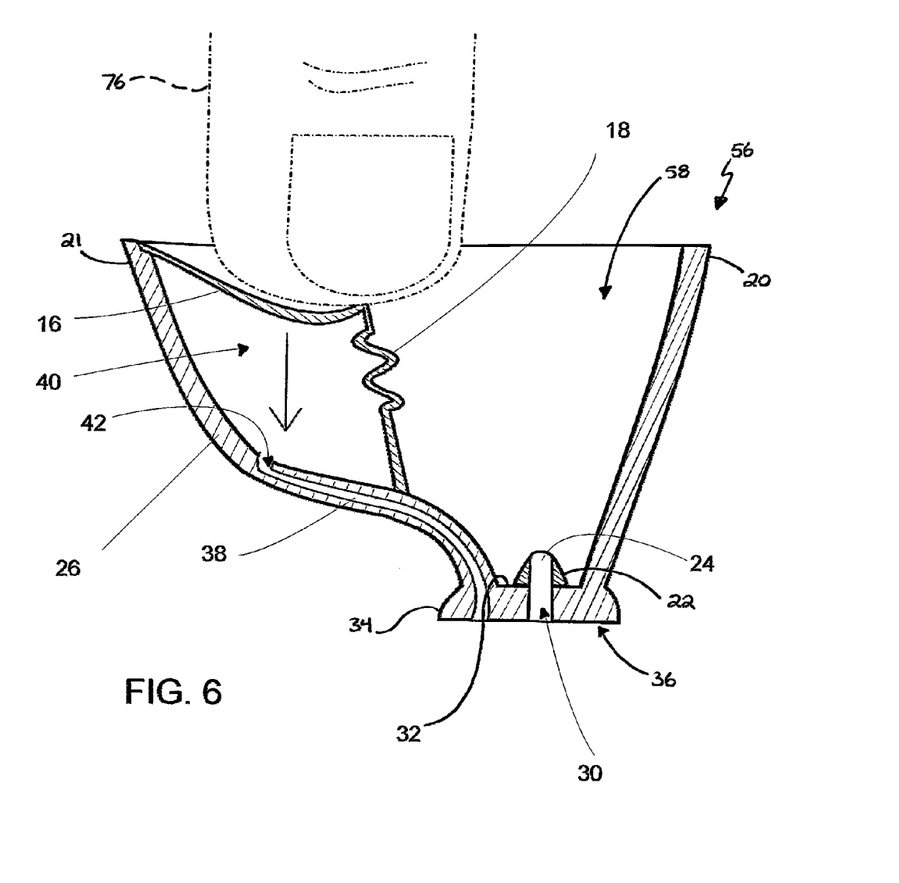
FIG. 6 is a further cross-sectional view thereof, illustrating a finger of the user selectively depressing a hollow chamber portion of the present invention, in at least one embodiment.

In a bit more detail, during use, with the ear plug 56 seated in the ear 62 of the user 60, the combination of the relatively small opening 24 of the sound hole 30 along with the back pressure naturally exerted by the column of air in the ear canal 72 protects against water entering the sound hole 30. Should the ear plug 56 encounter a substantial amount of water, such as when the ear plug 56 is temporarily submerged, the main cavity 58 would fill with water; however, when the ear plug 56 should subsequently emerge from out of the water, most of the water would naturally drain out of the main cavity 58 due to gravity and the shape of the ear plug body 26—leaving behind only droplets of water clinging to the main cavity 58 due to the strong adhesion and cohesion properties of water. As mentioned above, the dimensions of the sound hole body 22, in at least one embodiment, assist in substantially preventing any water droplets from covering the opening 24 of the sound hole 30, given that the sound hole body 22 elevates the opening 24 of the sound hole 30 a distance above the base 32 of the main cavity 58, thereby offsetting the water's cohesion property that would otherwise form a contiguous layer of water across the base 32 and opening 24 if the opening 24 were on the same plane as the base 32. With the opening 24 being elevated above the base 32 of the main cavity 58, the volume of water droplets that might nevertheless gather on and around the opening 24 is relatively minimal, such that the droplets are able to be cleared with relative ease. To clear such occluding droplets, the user 60 simply compresses the air chamber 40 by pushing or depressing the top portion 16 of the air chamber 40 with their finger 76 (FIG. 6), thereby temporarily collapsing the chamber wall 18 and displacing a volume of air in the air chamber 40. The displaced air exits out of the air chamber 40 through the chamber hole 42, travels through the air channel 38, and into the ear canal 72. The displacement of air continues as it seeks to reach equilibrium by exiting the ear canal 72 through a path of least resistance, which is through the sound hole 30 and to the outside air through the opening 24. As the displaced air exits out the opening 24, any occlusions to the opening 24 (including water droplets) will be cleared and the hearing level will be restored. As the user 60 removes their finger 76, the top portion 16 and chamber wall 18 will resume their original static shapes and, as they do, air will be drawn back into the air chamber 40 from outside the ear plug 56, following in the reverse path of the originally displaced air. The ear plug 56 will then be completely back to its static position prior to the submersion, with the occlusions removed and the hearing level restored.

Figure 9:
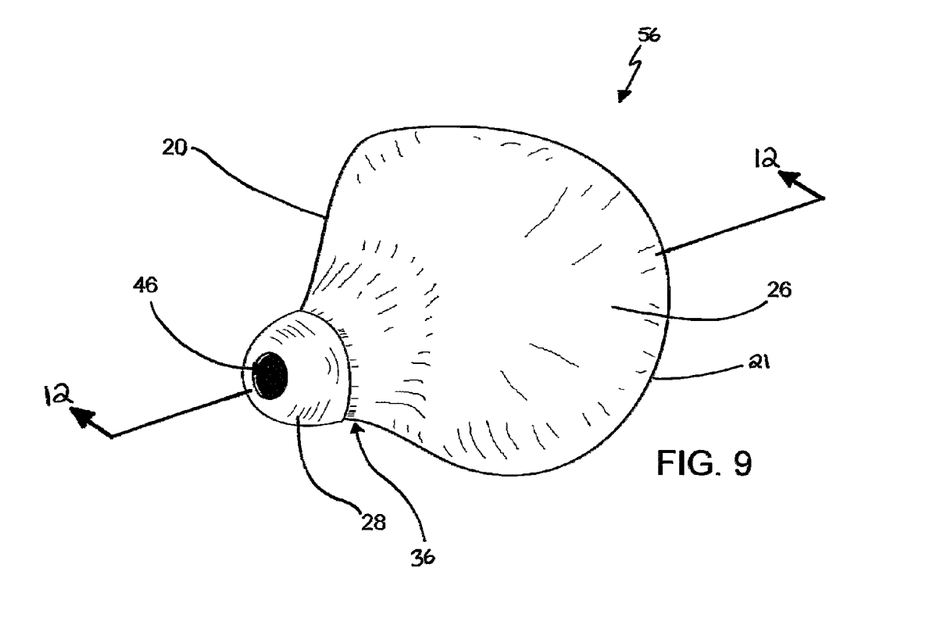
FIG. 9 is a bottom perspective view of a further embodiment of the present invention, in at least one embodiment.
Figure 10:
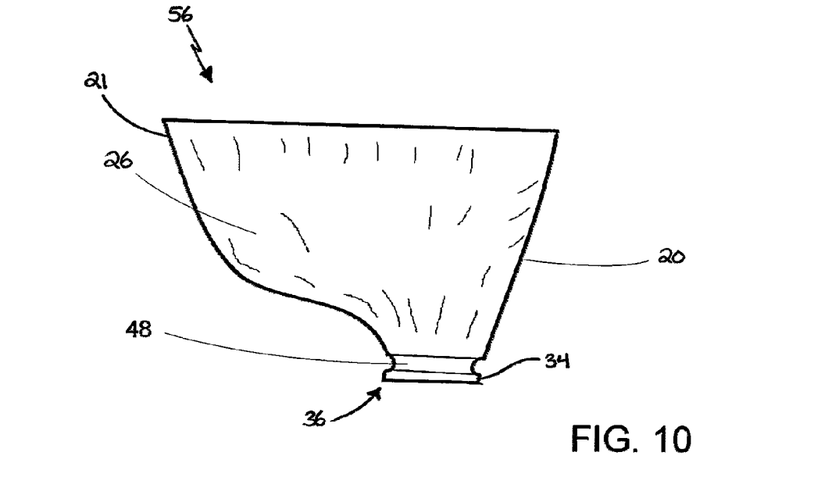
FIG. 10 is a side view thereof, in at least one embodiment.
Figure 11:
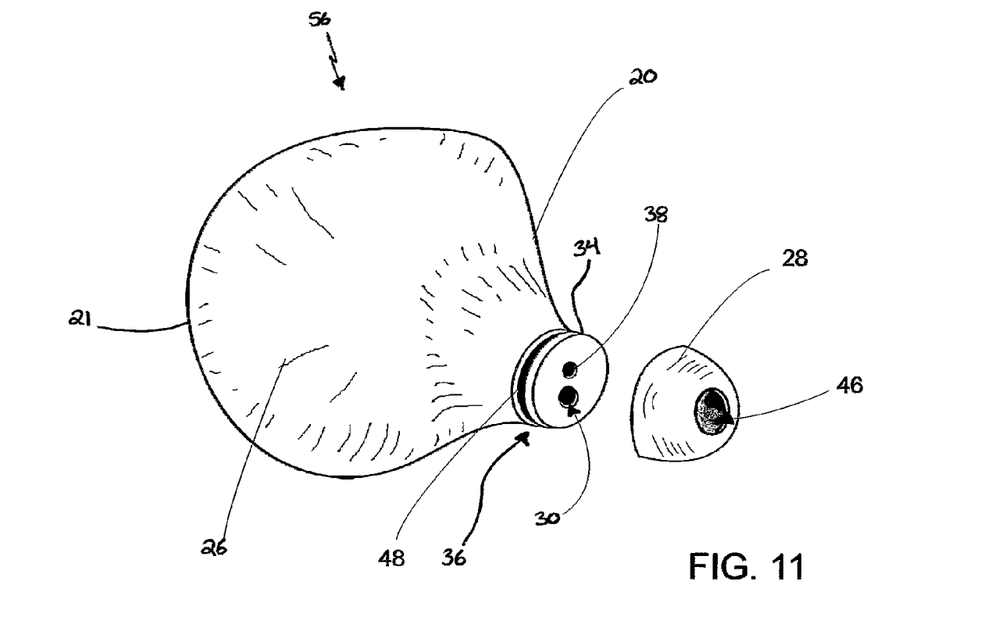
FIG. 11 is an exploded bottom perspective view thereof, in at least one embodiment.
Figure 14:
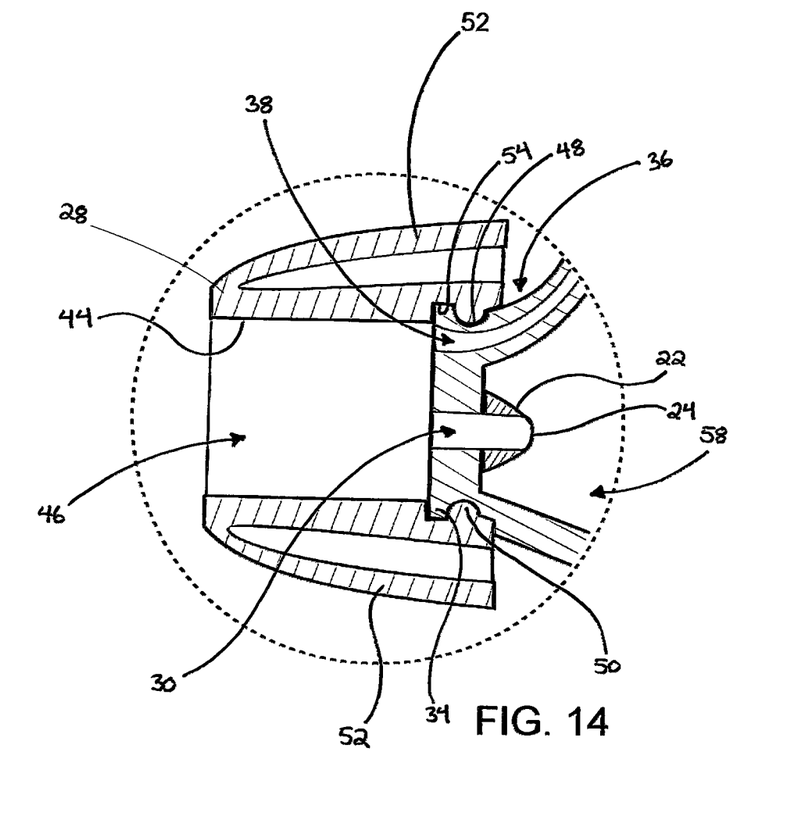
FIG. 14 is a similar enlarged view of a portion of the cross-sectional view of FIG. 12, but showing an alternative configuration of a removably attached ear tip, in at least one embodiment.

Referring now to FIGS. 9-11, in at least one embodiment, an ear tip 28 is removably engagable with the inner end 36 of the ear plug 56 and configured for improving the fit of the inner end 36 within the user's ear canal 72. In a bit more detail, the ear tip 28 is preferably rounded and conical in shape for being inserted into the ear canal 72 with relative ease, and provides a tip hole 46 extending therethrough for maintaining fluid communication between the ear canal 72 and the air outside the ear plug 56. However, in further embodiments, the ear tip 28 may take on any other shape, dimension or configuration, now known or later developed, that enable it to substantially carry out the functionality herein described. One such further embodiment, as discussed below, is shown in FIG. 14. Furthermore, the inner end 36 of the ear plug 56 is preferably capable of removably receiving a wide variety of ear tips 28, thereby allowing the user 60 to selectively interchange ear tips 28 for creating a custom, comfortable fit for their particular ear canal 72 dimensions. In that regard, while the ear tip 28 is preferably made of the same material as the ear plug 56, it may also be manufactured separately from the rest of the ear plug 56, using the same material or combination of materials as the ear plug 56, or relatively more flexible materials, such as silicone. However, similar to the ear plug 56, the ear tip 28 may be made of any material or combination of materials, now known or later developed, capable of allowing the ear tip 28 to substantially carry out the functionality herein described. In still further embodiments, the ear tip 28 may be permanently engaged or otherwise integral with the inner end 36 of the ear plug 56.

Figure 12:
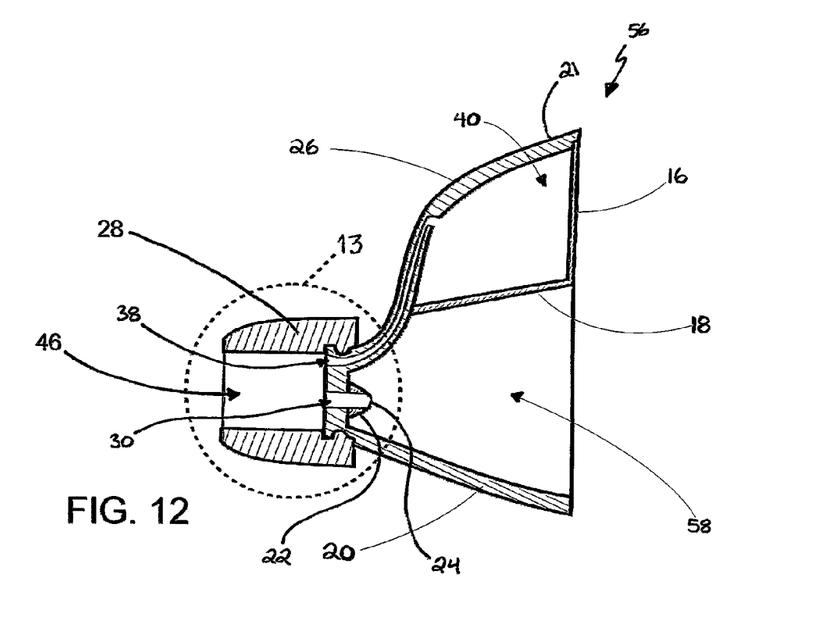
FIG. 12 is a cross-sectional view thereof, taken along line 12-12 in FIG. 9, in at least one embodiment.
Figure 13:
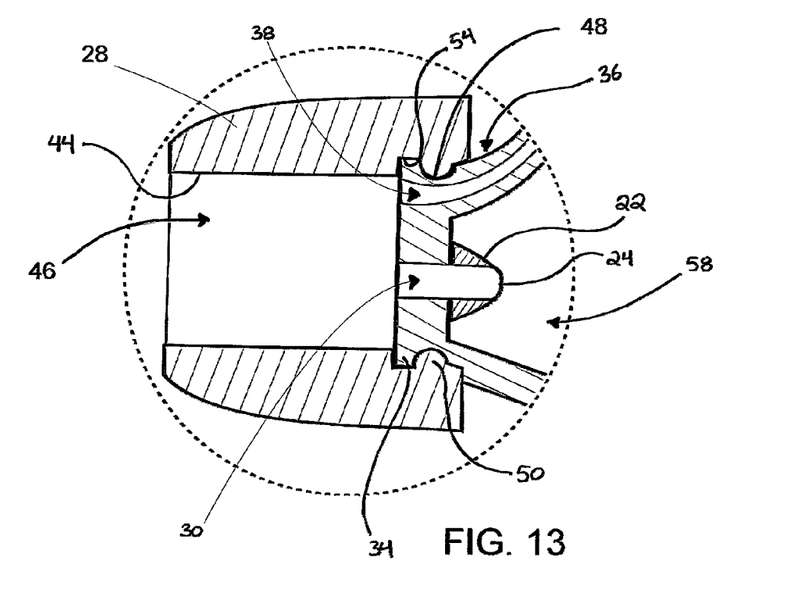
FIG. 13 is an enlarged view of a portion of the cross-sectional view of FIG. 12, in at least one embodiment.

With continued reference to the embodiment shown in FIG. 11, and as more clearly illustrated in the cross-sectional views of FIGS. 12 and 13, the inner end 36 of the ear plug 56 preferably provides an at least one annular groove 48 sized and configured for selectively mating with a corresponding at least one annular rib 50 positioned on an inner surface 44 of the tip hole 46. Thus, in such an embodiment, an inner diameter of the tip hole 46 is sized for approximating an outer diameter of the inner end 36, allowing the ear tip 28 to be engaged over the inner end 36. In this way, each of the sound hole 30 and air channel 38 is in fluid communication with the tip hole 46 and remains unobstructed. In embodiments where the inner end 36 provides the flange 34, the inner surface 44 of the tip hole 46 further provides an annular flange groove 54 sized and configured for selectively mating with the flange 34. In further embodiments, one or more of the annular groove 48, annular rib 50, flange 34, and flange groove 54 may be omitted, with the resulting selective engagement between the inner end 36 and ear tip 28 being more of an interference fit. In still further embodiments, any other means, now known or later developed, for enabling selective engagement between the inner end 36 and ear tip 28 may be substituted.

As mentioned above, an alternate embodiment of the ear tip 28 is shown in FIG. 14. In a bit more detail, this particular embodiment of the ear tip 28 provides a hollow cone portion 52 configured for being selectively radially deformable as it is inserted into the ear canal 72, thus allowing the ear tip 28 to selectively conform to and fit within a relatively wider range of ear canal 72 shapes and sizes. Additionally, once positioned within the ear canal 72, the cone portion 52 tends to deflect flat against the ear canal 72 for providing a relatively large contact area therewith for better sealing out water and air.

To summarize, regarding the exemplary embodiments of the present invention as shown and described herein, it will be appreciated that a water sports ear plug is disclosed and configured for protecting a user's ear canal from coming into contact with water and wind, while also consistently allowing sound to pass therethrough. Because the principles of the invention may be practiced in a number of configurations beyond those shown and described, it is to be understood that the invention is not in any way limited by the exemplary embodiments, but is generally directed to a water sports ear plug and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention. Furthermore, the various features of each of the above-described embodiments may be combined in any logical manner and are intended to be included within the scope of the present invention.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor believes that the claimed subject matter is the invention.

What is claimed is:

1. An ear plug for use in an ear of a user during water-related activities, the ear plug comprising:
    an ear plug body adapted to fit against a cavum conchae of the ear, the ear plug body defining a main cavity therewithin, configured for opening outwardly away from the ear;
    an inner end of the ear plug body sized and configured for fitting into an ear canal of the ear;
    a base of the main cavity defining a sound hole that extends down through each of the base and inner end of the ear plug body;
    a chamber wall positioned within and extending across the main cavity, forming a hollow air chamber between the chamber wall and a side of the ear plug body, the air chamber in fluid communication with the sound hole; and
    a selectively deformable top portion extending overtop of and enclosing the air chamber;
    whereby, during use, with the ear plug seated in the ear of the user, the air chamber is capable of selectively clearing any water droplets that may enter the main cavity and obstruct the sound hole, thereby protecting the ear canal from coming into contact with water and wind, while also consistently allowing sound to pass therethrough.

2. The ear plug of claim 1, wherein the ear plug body is substantially conical-shaped.

3. The ear plug of claim 1, wherein an opening of the sound hole is positioned within the main cavity and elevated a distance above the base.

4. The ear plug of claim 3, wherein the opening of the sound hole has a diameter of not more than 0.762 millimeters.

5. The ear plug of claim 3, wherein the base of the main cavity provides an upwardly protruding sound hole body through which the sound hole extends, thereby elevating the opening of the sound hole a distance above the base.

6. The ear plug of claim 5, wherein the sound hole body is substantially conical-shaped.

7. The ear plug of claim 5, wherein the sound hole body has a height of between one millimeter and five millimeters.

8. The ear plug of claim 1, wherein a first side of the ear plug body is adapted to rest against a tragus of the ear, while an opposing second side of the ear plug body is adapted to rest against an antihelix of the ear.

9. The ear plug of claim 8, wherein the air chamber is formed between the chamber wall and the second side of the ear plug body, adjacent the antihelix of the ear.

10. The ear plug of claim 1, wherein the ear plug is made of a relatively soft, resilient material.

11. The ear plug of claim 1, wherein the chamber wall is selectively deformable.

12. The ear plug of claim 1, wherein the inner end of the ear plug body is relatively flat.

13. The ear plug of claim 1, wherein the inner end of the ear plug body provides an at least one external flange sized and configured for snugly fitting into and frictionally contacting the ear canal.

14. The ear plug of claim 1, wherein the ear plug body further comprises an air channel extending from the air chamber down through the inner end of the ear plug body for allowing air to selectively travel from the air chamber down into the ear canal, and up through the sound hole.

15. The ear plug of claim 1, further comprising an ear tip removably engagable with the inner end of the ear plug body and configured for improving the fit of the inner end within the ear canal, the ear tip providing a tip hole extending therethrough for maintaining fluid communication between the ear canal and the air outside the ear plug.

16. The ear plug of claim 15, wherein the ear tip provides a hollow cone portion configured for being selectively radially deformable as it is inserted into the ear canal, thus allowing the ear tip to selectively conform to and fit within a relatively wider range of ear canal shapes and sizes.

17. The ear plug of claim 15, wherein an inner diameter of the tip hole is sized for approximating an outer diameter of the inner end, allowing the ear tip to be engaged over the inner end.

18. The ear plug of claim 17, wherein the inner end of the ear plug body provides an at least one annular groove sized and configured for selectively mating with a corresponding at least one annular rib positioned on an inner surface of the tip hole, thereby strengthening the engagement between the ear tip and the inner end.

19. An ear plug for use in an ear of a user during water-related activities, the ear plug comprising:
- a substantially hollow, inwardly extending, conical-shaped ear plug body adapted to fit against a cavum conchae of the ear, the ear plug body defining a main cavity therewithin, configured for opening outwardly away from the ear;
- an inner end of the ear plug body sized and configured for fitting into an ear canal of the ear;
- a base of the main cavity providing an upwardly protruding sound hole body, the sound hole body defining a sound hole that extends down through each of the sound hole body, base and inner end of the ear plug body, with an opening of the sound hole being elevated a distance above the base;
- a chamber wall positioned within and extending across the main cavity, forming a hollow air chamber between the chamber wall and a side of the ear plug body, the air chamber in fluid communication with the sound hole; and
- a selectively deformable top portion extending overtop of and enclosing the air chamber;
- whereby, during use, with the ear plug seated in the ear of the user, the position of the opening of the sound hole relative to the base of the main cavity assists in substantially preventing any water droplets that may enter the main cavity from obstructing the opening, while the air chamber is capable of selectively clearing any water droplets that may nevertheless obstruct the opening, thereby protecting the ear canal from coming into contact with water and wind, while also consistently allowing sound to pass therethrough.

\* \* \* \* \*